US011426205B2

(12) United States Patent
Mantzaris et al.

(10) Patent No.: US 11,426,205 B2
(45) Date of Patent: Aug. 30, 2022

(54) SYNDESMOSIS TREATMENT CONSTRUCT

(71) Applicant: In2Bones USA, LLC, Memphis, TN (US)

(72) Inventors: Adam Mantzaris, Memphis, TN (US); Rebecca Hawkins Wahl, Escondido, CA (US); Brandon Beckendorf, Memphis, TN (US)

(73) Assignee: In2Bones USA, LLC, Memphis, TN (US)

( * ) Notice: Subject to any disclaimer, the term of this patent is extended or adjusted under 35 U.S.C. 154(b) by 648 days.

(21) Appl. No.: 16/505,509

(22) Filed: Jul. 8, 2019

(65) Prior Publication Data

US 2020/0022730 A1 Jan. 23, 2020

Related U.S. Application Data

(60) Provisional application No. 62/699,617, filed on Jul. 17, 2018.

(51) Int. Cl.
| | |
|---|---|
| *A61B 17/68* | (2006.01) |
| *A61B 17/04* | (2006.01) |
| *A61B 17/56* | (2006.01) |
| *A61F 2/30* | (2006.01) |
| *A61F 2/08* | (2006.01) |
| *A61F 2/42* | (2006.01) |

(52) U.S. Cl.
CPC .......... *A61B 17/683* (2013.01); *A61F 2/4202* (2013.01); *A61B 2017/0404* (2013.01); *A61B 2017/564* (2013.01); *A61F 2002/0882* (2013.01); *A61F 2002/30622* (2013.01); *A61F 2002/30672* (2013.01)

(58) Field of Classification Search
CPC ............ A61B 17/683; A61B 2017/564; A61B 2017/0404; A61F 2002/0882; A61F 2002/30622; A61F 2002/30672
See application file for complete search history.

(56) References Cited

U.S. PATENT DOCUMENTS

2017/0209140 A1* 7/2017 Thornes ............... A61B 17/068

* cited by examiner

*Primary Examiner* — Wade Miles
*Assistant Examiner* — Mohammed S Adam
(74) *Attorney, Agent, or Firm* — Rutan & Tucker LLP; Hani Z. Sayed

(57) ABSTRACT

An apparatus and method are provided for a syndesmosis treatment construct configured to be placed into a cinched configuration that presses a first bone against a second bone. The syndesmosis treatment construct comprises a proximal fixator to contact the first bone and a distal fixator to contact the second bone. A first suture and a second suture are parallelly looped through the proximal fixator and oppositely looped through the distal fixator. Distal ends of the first and second sutures are fixated within a washer disposed between the proximal fixator and the first bone. Proximal ends of the first and second sutures are passed through openings in the washer and through the proximal fixator. Pulling of the proximal ends by a practitioner places the syndesmosis treatment construct into a cinched configuration. Any of various suitable suture knots may be formed so as to fixate the cinched configuration.

18 Claims, 5 Drawing Sheets

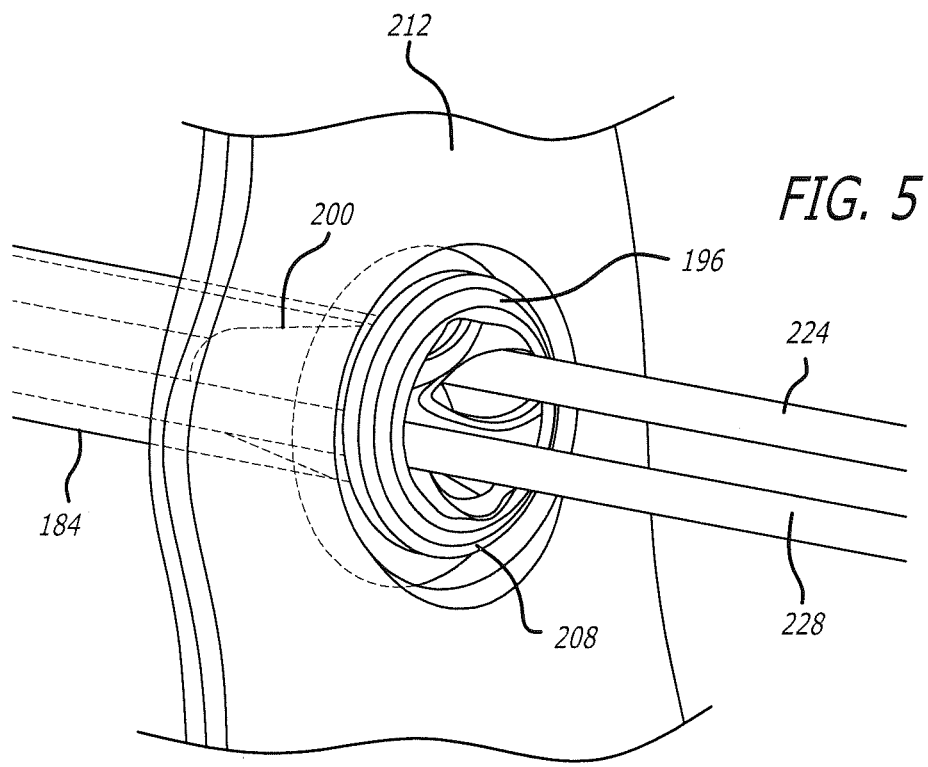
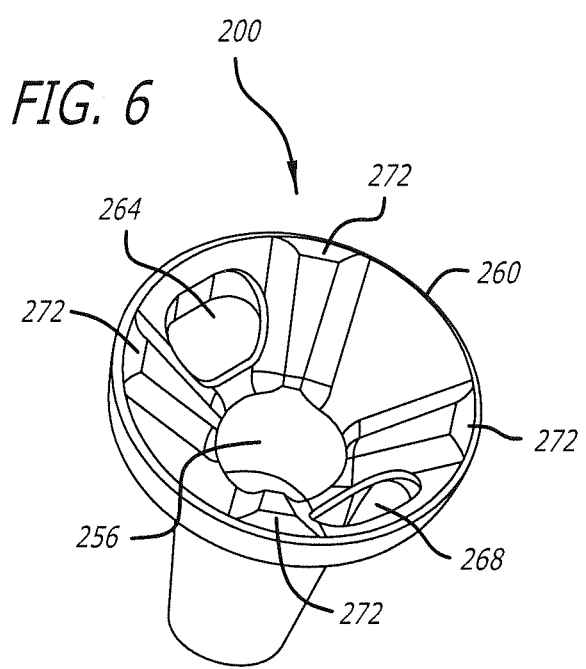
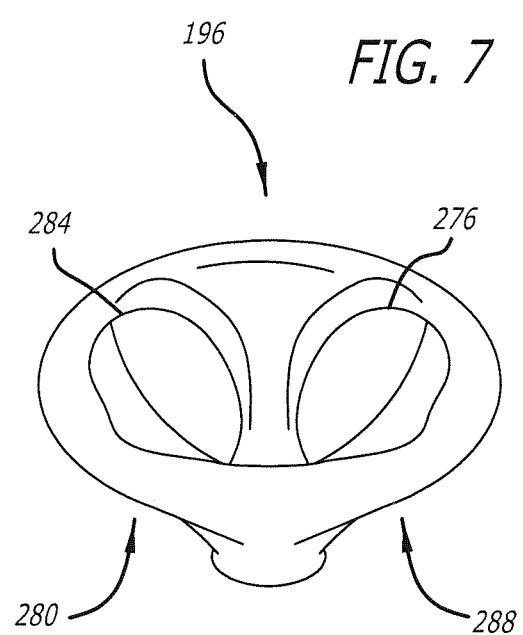

SYNDESMOSIS TREATMENT CONSTRUCT

PRIORITY

This application claims the benefit of and priority to U.S. Provisional Application, entitled "Syndesmosis Treatment Construct," filed on Jul. 17, 2018 and having application Ser. No. 62/699,617, the entirety of said application being incorporated herein by reference.

FIELD

Embodiments of the present disclosure generally relate to the field of securing bones together. More specifically, embodiments of the disclosure relate to systems and methods for a syndesmosis treatment construct configured to be placed into a cinched configuration that secures a first bone against a second bone.

BACKGROUND

A syndesmosis is a slightly movable fibrous joint in which bones such as the tibia and fibula are joined together by connective tissue. The distal tibia fibular joint and the radioulnar joint are examples of syndesmoses. Injuries to the ankle syndesmosis are common and frequently occur in patients having ankle fractures.

Due to the complex biomechanics of ankle syndesmosis injuries and the relatively increased healing time associated with them, there has been widespread debate on both the strongest and most appropriate methods of fixation when treated operatively. Conventional treatments for ankle syndesmosis injuries include metallic or bioabsorbable screw fixation, as well as various methods of suture button fixation. A benefit of suture button fixation treatments is that they generally do not require additional procedures for removal of implants as do screw fixation treatments.

There is an ongoing need for the development of bone fusion capabilities such as that related to, for example, treating injuries to the ankle syndesmosis. Provided herein are embodiments and methods for a syndesmosis treatment construct configured to be placed into a cinched configuration that presses a first bone against a second bone.

SUMMARY

An apparatus and method are provided for a syndesmosis treatment construct configured to be passed through a bone hole across a first bone and a second bone and placed into a cinched configuration whereby the first bone and the second bone are pressed together. The syndesmosis treatment construct comprises a proximal fixator configured to contact the first bone and a distal fixator configured to contact the second bone. A first suture and a second suture are parallelly looped through the proximal fixator and oppositely looped through the distal fixator such that a proximal end of the first suture and a proximal end of the second suture extend from the proximal fixator. A washer is disposed between the first bone and the proximal fixator and is configured to fixate a distal end of the first suture and a distal end of the second suture, such that pulling on the proximal end of the first suture and the proximal end of the second suture places the syndesmosis treatment construct into the cinched configuration.

In an exemplary embodiment, a syndesmosis treatment construct configured to be passed through a bone hole across a first bone and a second bone and placed into a cinched configuration whereby the first bone and the second bone are pressed together comprises: a proximal fixator configured to contact the first bone; a distal fixator configured to contact the second bone; a first suture and a second suture parallelly looped through the proximal fixator and oppositely looped through the distal fixator such that a proximal end of the first suture and a proximal end of the second suture extend from the proximal fixator; and a washer disposed between the first bone and the proximal fixator and configured to fixate a distal end of the first suture and a distal end of the second suture, such that pulling on the proximal end of the first suture and the proximal end of the second suture causes the cinched configuration.

In another exemplary embodiment, the proximal fixator and the washer are configured to be seated within an aperture of a bone fusion plate. In another exemplary embodiment, the proximal fixator is a cone-shaped member configured to contact a disk portion comprising the washer, the disk portion being configured to contact bone in lieu of being seated within the aperture.

In another exemplary embodiment, the proximal fixator includes a first aperture, a second aperture, a third aperture and a fourth aperture that are configured to facilitate a practitioner forming various surgical knots to maintain the cinched configuration. In another exemplary embodiment, the proximal end of the first suture is drawn proximally through the first aperture and passed distally through the fourth aperture before exiting between the washer and the proximal fixator, and wherein the proximal end of the second suture is drawn proximally through the second aperture and passed through the third aperture before exiting between the washer and the proximal fixator, the exiting proximal end of the first suture and the exiting proximal end of the second suture being configured to facilitate a practitioner forming any of various surgical knots to maintain the cinched configuration.

In another exemplary embodiment, the washer is a cone-shaped member including a disk portion with a centrally disposed countersunk hole that is configured to fixate the distal end of the first suture and the distal end of the second suture. In another exemplary embodiment, the countersunk hole is configured to receive a compressible sleeve that is crimped onto the distal end of the first suture and the distal end of the second suture, such that the distal end of the first suture and the distal end of the second suture are fixated with respect to the washer. In another exemplary embodiment, the disk portion includes a first suture passthrough and a second suture passthrough disposed on opposite sides of the washer and configured to allow the proximal end of the first suture and the proximal end of the second suture to extend through the washer. In another exemplary embodiment, the disk portion includes multiple raised portions extending radially from the countersunk hole to the periphery of the disk portion. In another exemplary embodiment, the raised portions are configured to a contact surface for the proximal fixator in the cinched configuration. In another exemplary embodiment, the raised portions are configured to provide a space between the proximal fixator and the washer through which the proximal end of the first suture and the proximal end of the second may be passed.

In another exemplary embodiment, the distal fixator comprises an oblong-shaped member having a first aperture and a second aperture and is configured to be drawn through the bone hole before the first bone and the second bone are cinched together. In another exemplary embodiment, the first suture extends distally through the first aperture and extends proximally through the second aperture, and wherein the second suture extends distally through the second aperture and then extends proximally through the first aperture. In another exemplary embodiment, the first suture and the second suture loop oppositely through the first aperture and the second aperture to inhibit rotation of the distal fixator during cinching the syndesmosis treatment construct.

In an exemplary embodiment, a method for syndesmosis treatment construct configured to be passed through a bone hole across a first bone and a second bone and placed into a cinched configuration whereby the first bone and the second bone are pressed together comprises: configuring a proximal fixator to contact the first bone; configuring a distal fixator to contact the second bone; looping a first suture and a second suture parallelly through the proximal fixator and oppositely through the distal fixator, such that a proximal end of the first suture and a proximal end of the second suture extend from the proximal fixator; configuring a washer to fixate a distal end of the first suture and a distal end of the second suture; and disposing the washer between the first bone and the proximal fixator such that pulling on the proximal end of the first suture and the proximal end of the second suture causes the cinched configuration.

In another exemplary embodiment, configuring the washer includes forming a disk portion of the washer to be seated either within an aperture of a bone fusion plate or in contact with the first bone in absence of the bone fusion plate. In another exemplary embodiment, configuring the proximal fixator includes forming a first aperture, a second aperture, a third aperture and a fourth aperture to facilitate a practitioner forming various surgical knots to maintain the cinched configuration. In another exemplary embodiment, configuring the distal fixator includes forming an oblong-shaped member having a first aperture and a second aperture that is suitable to be drawn through the bone hole before the first bone and the second bone are cinched together.

BRIEF DESCRIPTION OF THE DRAWINGS

The drawings refer to embodiments of the present disclosure in which:

FIG. 5 illustrates the proximal fixator and washer of FIG. 4 seated with an aperture of a bone fusion plate, according to the present disclosure;

FIG. 6 illustrates a close-up isometric view of a washer, according to the present disclosure;

FIG. 7 illustrates a close-up isometric view of a proximal fixator in accordance with the present disclosure.

Figure 1:
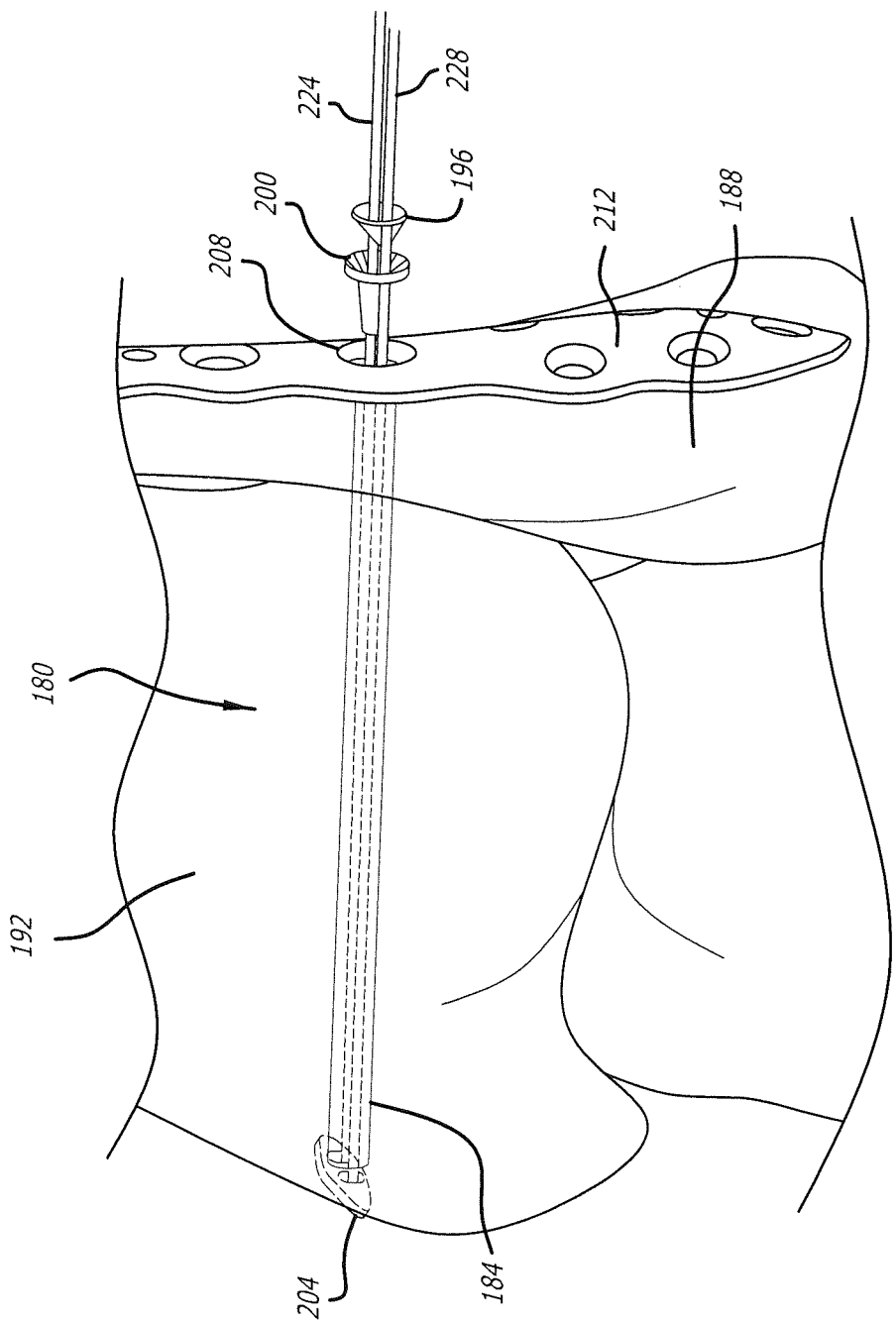
FIG. 1 illustrates an exemplary use environment wherein an exemplary embodiment of a syndesmosis treatment construct is disposed within a bone hole and pressing a first bone and a second bone together, in accordance with the present disclosure.

While the present disclosure is subject to various modifications and alternative forms, specific embodiments thereof have been shown by way of example in the drawings and will herein be described in detail. The invention should be understood to not be limited to the particular forms disclosed, but on the contrary, the intention is to cover all modifications, equivalents, and alternatives falling within the spirit and scope of the present disclosure.

DETAILED DESCRIPTION

In the following description, numerous specific details are set forth in order to provide a thorough understanding of the present disclosure. It will be apparent, however, to one of ordinary skill in the art that the invention disclosed herein may be practiced without these specific details. In other instances, specific numeric references such as "first suture," may be made. However, the specific numeric reference should not be interpreted as a literal sequential order but rather interpreted that the "first suture" is different than a "second suture." Thus, the specific details set forth are merely exemplary. The specific details may be varied from and still be contemplated to be within the spirit and scope of the present disclosure. The term "coupled" is defined as meaning connected either directly to the component or indirectly to the component through another component. Further, as used herein, the terms "about," "approximately," or "substantially" for any numerical values or ranges indicate a suitable dimensional tolerance that allows the part or collection of components to function for its intended purpose as described herein.

A syndesmosis is a slightly movable fibrous joint in which bones such as the tibia and fibula are joined together by connective tissue. The distal tibia fibular joint and the radioulnar joint are examples of syndesmoses. Injuries to the ankle syndesmosis are common and frequently occur in patients having ankle fractures. There is an ongoing need for the development of bone fusion capabilities such as that found in, for example, treating injuries to the ankle syndesmosis. Provided herein are embodiments and methods for a syndesmosis treatment construct configured to be placed into a cinched configuration that presses a first bone against a second bone.

FIG. 1 illustrates an exemplary use environment wherein an exemplary embodiment of a syndesmosis treatment construct 180 is disposed within a bone hole 184 and pressing a first bone 188 and a second bone 192 together, in accordance with the present disclosure. The syndesmosis treatment construct 180 comprises a proximal fixator 196 and a washer 200 that are configured to contact the first bone 184, and a distal fixator 204 that is configured to contact the second bone 192. In the embodiment illustrated in FIG. 1, the proximal fixator 196 and the washer 200 are seated within an aperture 208 of a bone fusion plate 212. Although the bone fusion plate 212 desirably provides support for the proximal fixator 196 and the washer 200, the bone fusion plate 212 may be omitted without limitation and the proximal fixator 196 and the washer 200 may contact the first bone 188, as desired. Further, it should be understood that the washer 200 is an optional component that may be omitted, in some embodiments, and the proximal fixator 196 may be placed directly in contact with the first bone 188 or the bone fusion plate 212, as needed.

The proximal fixator 196 is generally a round, cone-shaped member suitable for contacting bone, and the distal fixator 204 is an oblong-shaped member suitable for contacting bone. As will be appreciated, the oblong-shape of the distal fixator 204 is configured to be drawn through the bone hole 184 before the first and second bones 188, 192 are cinched together. In general, however, the proximal and distal fixators 196, 204 may include any of various shapes that are found to be advantageous for pressing bones together, without limitation.

Figure 2A:
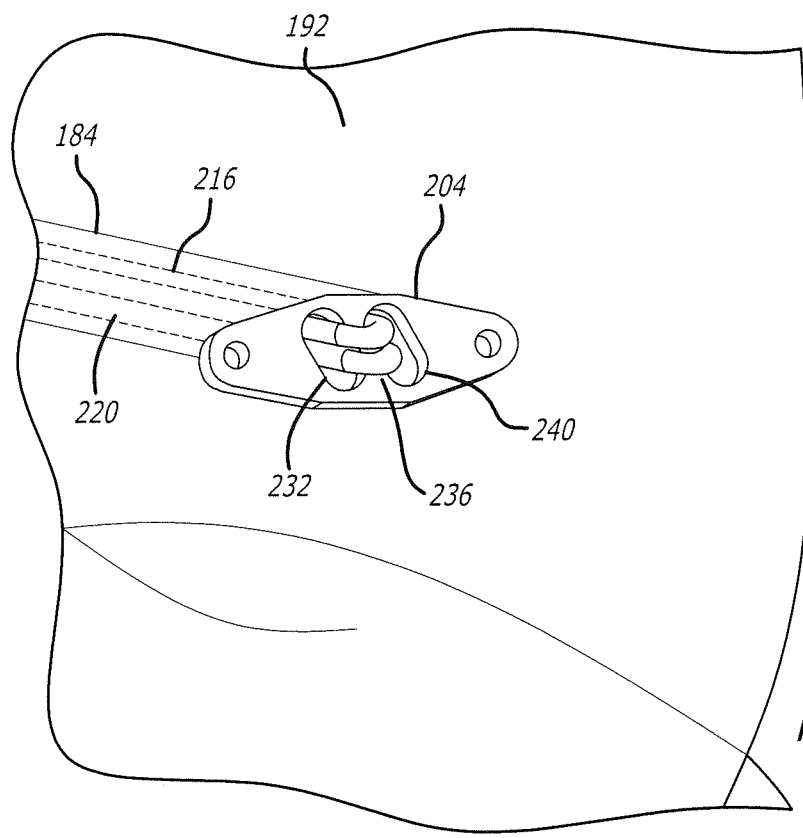
FIG. 2A illustrates a distal portion of the syndesmosis treatment construct of FIG. 1, according to the present disclosure.
Figure 2B:
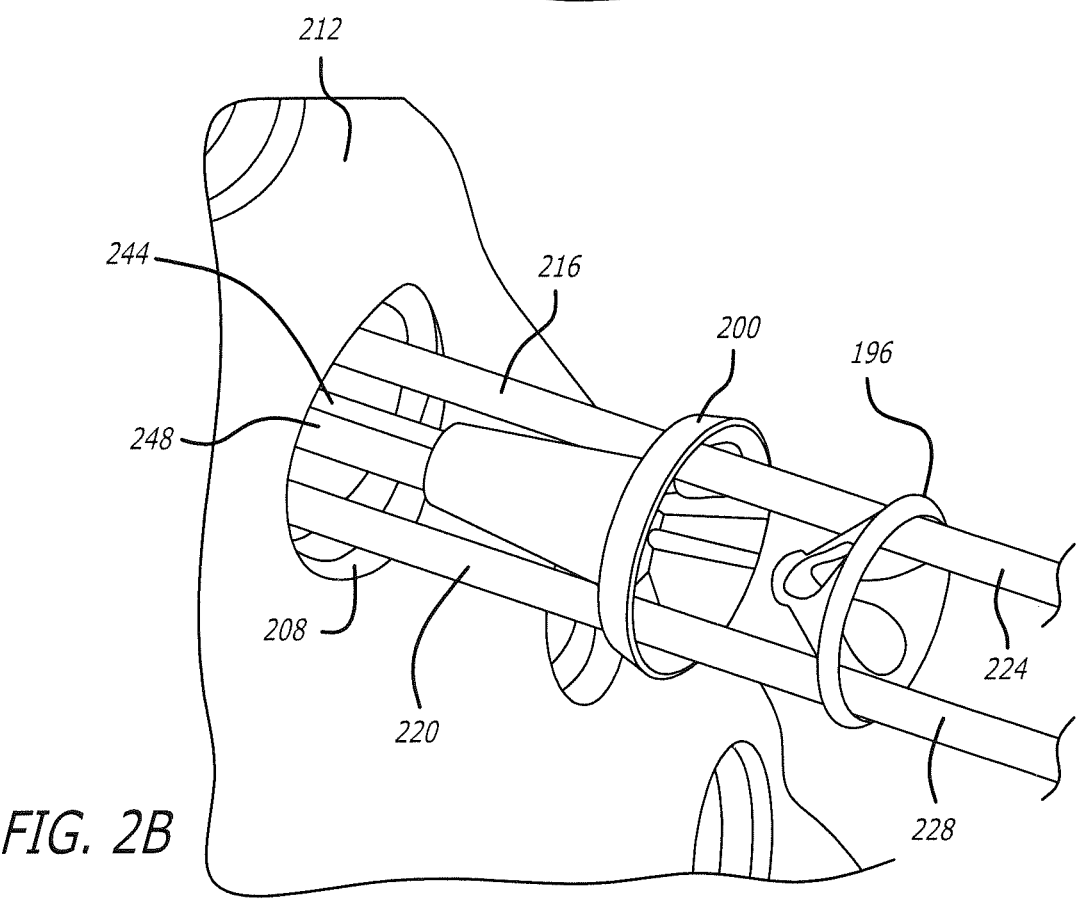
FIG. 2B illustrates a proximal portion of the syndesmosis treatment construct of FIG. 1, in accordance with the present disclosure.

FIGS. 2A and 2B illustrate closer views of the distal fixator 204 and the proximal fixator 196, respectively. As shown in FIGS. 2A-2B, the syndesmosis treatment construct 180 includes a first suture 216 and a second suture 220 that are parallelly looped through the proximal fixator 196, the washer 200 and the distal fixator 204 such that a proximal end 224 of the first suture 216 and a proximal end 228 of the second suture 220 extend from the proximal fixator 196. The proximal ends 224, 228 extending from the proximal fixator 196 enable the surgeon to pull on the first and second sutures 216, 220 to place the syndesmosis treatment construct 180 into the cinched configuration shown in FIG. 1. As will be appreciated, the first and second sutures 216, 220 are generally comprised of any of various suture materials that are suitable for syndesmosis treatment.

Figure 3:
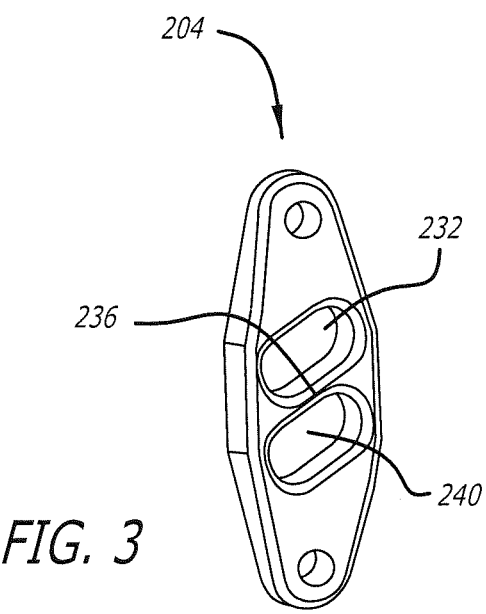
FIG. 3 illustrates a close-up isometric view of a distal fixator, according to the present disclosure.

With continuing reference to FIG. 2A, although the first and second sutures 216, 220 are parallelly looped through the proximal and distal fixators 196, 204, as disclosed hereinabove, the first and second sutures 216, 220 are looped in opposite directions. As such, the first suture 216 extends distally through a first aperture 232 comprising the distal fixator 204. The first suture 216 loops around a bar 236, shown in FIG. 3, and extends proximally through a second aperture 240 of the distal fixator 204. The second suture 220 extends distally through the second aperture 240, loops around the bar 236 and then extends proximally through the first aperture 232. It is contemplated that looping the first and second sutures 216, 220 in opposite directions serves to inhibit an undesirable rotation of the distal fixator 204 upon cinching the syndesmosis treatment construct 180, as shown in FIG. 1.

Figure 4:
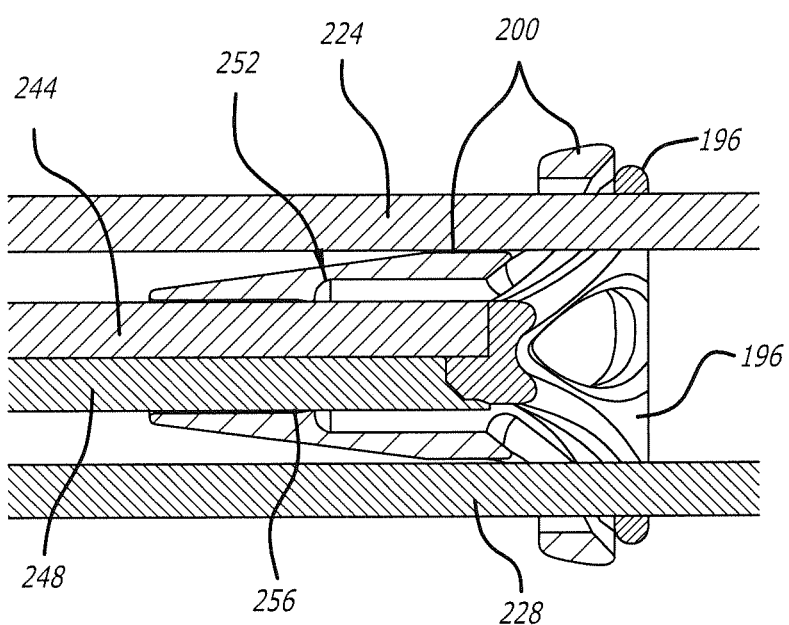
FIG. 4 illustrates a cross-sectional view of a proximal fixator engaged with a washer according to the present disclosure.

Turning now to FIG. 2B, in general the proximal fixator 196 and the washer 200 cooperate with the distal fixator 204 to cinch the syndesmosis treatment construct 180 when the surgeon pulls on the proximal ends 224, 228. The proximal ends 224, 228 pass through apertures disposed in the proximal fixator 196 and the washer 200 while respective distal ends 244, 248 are fixated in the washer 200. In an embodiment shown in FIG. 4, the distal ends 244, 248 are fixated within a compressible sleeve 252 that is disposed within a countersunk hole 256 of the washer 200. Thus, with the distal ends 244, 248 effectively fixated in the washer 200, pulling on the proximal ends 224, 228 cinches the first and second sutures 216, 220 around the distal fixator 204, causing the washer 200 to be pulled into and seated within the aperture 208 of the bone fusion plate 212, as shown in FIG. 5. It is contemplated that once the syndesmosis treatment construct 180 is placed in the cinched configuration as shown in FIG. 5, the surgeon may form any of various suitable suture knots so as to fixate the cinched configuration.

FIG. 6 illustrates a close-up isometric view of the washer 200, according to the present disclosure. The washer 200 generally is a cone-shaped member that includes a disk portion 260 with a centrally disposed countersunk hole 256. As discussed above, the countersunk hole 256 is configured to fixate the distal ends 244, 248. In some embodiments, the countersunk hole 256 is configured to receive a compressible sleeve, such as the sleeve 252, that is crimped onto the distal ends 244, 248, such that the distal ends are fixated with respect to the washer 200.

In the illustrated embodiment of FIG. 6, the disk portion 260 includes a first suture passthrough 264 and a second suture passthrough 268 disposed on opposite sides of the washer 200. The first and second suture passthroughs 264, 268 respectively allow the proximal ends 224, 228 to extend from the bone hole 184, through the washer 200 and to the proximal fixator 196. Further, multiple raised portions 272 are disposed in the disk portion 260, extending radially from the countersunk hole 256 to the periphery of the disk portion 260. In some embodiments, the raised portions 272 provide structural integrity and a contact surface for the proximal fixator 196 when the syndesmosis treatment construct 180 is in the cinched configuration. In some embodiments, the raised portions 272 provide a space between the proximal fixator 196 and the washer 200 through which the sutures 216, 220 may passed during forming surgical knots. It is contemplated that the raised portions 272 advantageously prevent the sutures from being damaged due to being pinched between the proximal fixator 196 and the washer 200.

FIG. 7 illustrates a close-up isometric view of the proximal fixator 196 in accordance with the present disclosure. The proximal fixator 196 generally is a cone-shaped member configured to contact the washer 200 as shown in FIG. 5. In the illustrated embodiment of FIG. 7, the proximal fixator 196 includes a first aperture 276, a second aperture 280, a third aperture 284 and a fourth aperture 288. The first and second apertures 276, 280 are disposed on opposite sides of the proximal fixator 196, and the third and fourth apertures 284, 288 are also oppositely disposed on the proximal fixator. As will be appreciated, the apertures 276-288 are configured to facilitate the surgeon forming various surgical knots so as to maintain the cinched configuration of the syndesmosis treatment construction 180.

Figure 8:
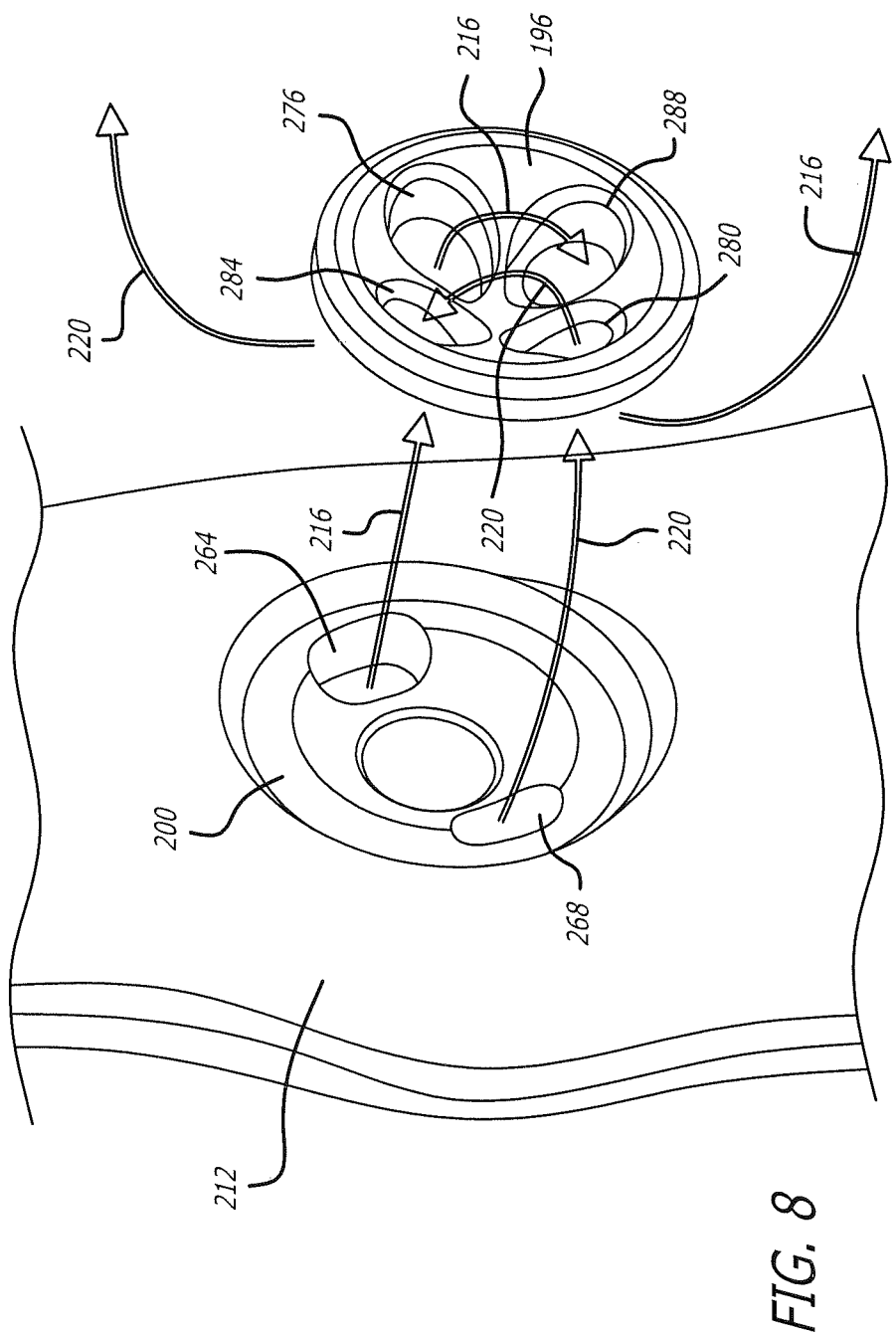
FIG. 8 illustrates an exemplary routing of a first suture and a second suture through the apertures of a proximal fixator.

An exemplary routing of the first and second sutures 216, 220 through the apertures 276-288 is illustrated in FIG. 8. The first suture 216, upon exiting the first suture passthrough 264 of the washer 200, is drawn proximally through the first aperture 276. Similarly, the second suture 220 exits the second suture passthrough 268 of the washer 200 and is drawn proximally through the second aperture 280. The sutures 216, 220 may be next drawn distally through adjacent apertures before being passed between the proximal fixator 196 and the disk portion 260 of the washer 200. In the embodiment illustrated in FIG. 8, the first suture 216 extends from the first aperture 276 and is drawn distally through the fourth aperture 288 while the second suture 220 extends from the second aperture 280 and is drawn distally through the third aperture 284. It should be understood that the order in which the first and second sutures 216, 220 are drawn through the apertures 276-288 is presented herein merely for the sake exposition and is not be construed as limiting in any way. It is contemplated, therefore, that the sutures 216, 220 may be threaded through the proximal fixator 196 by way of any of various suitable routes that may be found to be beneficial in practice. It is further contemplated that after drawing the first and second sutures 216, 220 through the proximal fixator 196, the surgeon may perform any of various surgical knots to lock the syndesmosis treatment construct 180 in the cinched configuration, as discussed hereinabove.

While the invention has been described in terms of particular variations and illustrative figures, those of ordinary skill in the art will recognize that the invention is not limited to the variations or figures described. In addition, where methods and steps described above indicate certain events occurring in certain order, those of ordinary skill in the art will recognize that the ordering of certain steps may be modified and that such modifications are in accordance with the variations of the invention. Additionally, certain of the steps may be performed concurrently in a parallel process when possible, as well as performed sequentially as described above. To the extent there are variations of the invention, which are within the spirit of the disclosure or equivalent to the inventions found in the claims, it is the intent that this patent will cover those variations as well. Therefore, the present disclosure is to be understood as not limited by the specific embodiments described herein, but only by scope of the appended claims.

What is claimed is:

1. A syndesmosis treatment construct configured to be passed through a bone hole across a first bone and a second bone and placed into a cinched configuration whereby the first bone and the second bone are pressed together, the syndesmosis treatment construct comprising:
    a proximal fixator configured to contact the first bone;
    a distal fixator configured to contact the second bone;
    a first suture and a second suture parallelly looped through the proximal fixator and oppositely looped through the distal fixator such that a proximal end of the first suture and a proximal end of the second suture extend from the proximal fixator; and
    a washer disposed between the first bone and the proximal fixator and configured to fixate a distal end of the first suture and a distal end of the second suture, such that pulling on the proximal end of the first suture and the proximal end of the second suture causes the cinched configuration; wherein the washer is a cone-shaped member.

2. The syndesmosis treatment construct of claim 1, wherein the proximal fixator and the washer are configured to be seated within an aperture of a bone fusion plate.

3. The syndesmosis treatment construct of claim 2, wherein the proximal fixator is a cone-shaped member configured to contact a disk portion comprising the washer, the disk portion being configured to contact bone in lieu of being seated within the aperture.

4. The syndesmosis treatment construct of claim 1, wherein the proximal fixator includes a first aperture, a second aperture, a third aperture and a fourth aperture that are configured to facilitate a practitioner forming various surgical knots to maintain the cinched configuration.

5. The syndesmosis treatment construct of claim 4, wherein the proximal end of the first suture is drawn proximally through the first aperture and passed distally through the fourth aperture before exiting between the washer and the proximal fixator, and wherein the proximal end of the second suture is drawn proximally through the second aperture and passed through the third aperture before exiting between the washer and the proximal fixator, the exiting proximal end of the first suture and the exiting proximal end of the second suture being configured to facilitate a practitioner forming any of various surgical knots to maintain the cinched configuration.

6. The syndesmosis treatment construct of claim 1, wherein the washer includes a disk portion with a centrally disposed countersunk hole that is configured to fixate the distal end of the first suture and the distal end of the second suture.

7. The syndesmosis treatment construct of claim 6, wherein the countersunk hole is configured to receive a compressible sleeve that is crimped onto the distal end of the first suture and the distal end of the second suture, such that the distal end of the first suture and the distal end of the second suture are fixated with respect to the washer.

8. The syndesmosis treatment construct of claim 6, wherein the disk portion includes a first suture passthrough and a second suture passthrough disposed on opposite sides of the washer and configured to allow the proximal end of the first suture and the proximal end of the second suture to extend through the washer.

9. The syndesmosis treatment construct of claim 6, wherein the disk portion includes multiple raised portions extending radially from the countersunk hole to a periphery of the disk portion.

10. The syndesmosis treatment construct of claim 9, wherein the raised portions are configured to contact a surface for the proximal fixator in the cinched configuration.

11. The syndesmosis treatment construct of claim 10, wherein the raised portions are configured to provide a space between the proximal fixator and the washer through which the proximal end of the first suture and the proximal end of the second suture may be passed.

12. The syndesmosis treatment construct of claim 1, wherein the distal fixator comprises an oblong-shaped member having a first aperture and a second aperture and is configured to be drawn through the bone hole before the first bone and the second bone are cinched together.

13. The syndesmosis treatment construct of claim 12, wherein the first suture extends distally through the first aperture and extends proximally through the second aperture, and wherein the second suture extends distally through the second aperture and then extends proximally through the first aperture.

14. The syndesmosis treatment construct of claim 13, wherein the first suture and the second suture loop oppositely through the first aperture and the second aperture to inhibit rotation of the distal fixator during cinching the syndesmosis treatment construct.

15. A method including the syndesmosis treatment construct of claim 1 for syndesmosis treatment construct configured to be passed through a bone hole across a first bone and a second bone and placed into a cinched configuration whereby the first bone and the second bone are pressed together, the method comprising:
    configuring the proximal fixator to contact the first bone;
    configuring the distal fixator to contact the second bone;
    looping the first suture and the second suture parallelly through the proximal fixator and oppositely through the distal fixator, such that the proximal end of the first suture and the proximal end of the second suture extend from the proximal fixator;
    configuring the washer to fixate the distal end of the first suture and the distal end of the second suture; and
    disposing the washer between the first bone and the proximal fixator such that pulling on the proximal end of the first suture and the proximal end of the second suture causes the cinched configuration.

16. The method of claim 15, wherein configuring the washer includes forming a disk portion of the washer to be seated either within an aperture of a bone fusion plate or in contact with the first bone in absence of the bone fusion plate.

17. The method of claim 15, wherein configuring the proximal fixator includes forming a first aperture, a second aperture, a third aperture and a fourth aperture to facilitate a practitioner forming various surgical knots to maintain the cinched configuration.

18. The method of claim 15, wherein configuring the distal fixator includes forming an oblong-shaped member having a first aperture and a second aperture that is suitable to be drawn through the bone hole before the first bone and the second bone are cinched together.

\* \* \* \* \*